United States Patent [19]

Wahl et al.

[11] 4,198,768
[45] Apr. 22, 1980

[54] ELECTRONICS ASSEMBLY EVALUATOR

[75] Inventors: Richard E. Wahl, Rochester; John E. King, Fairport; William C. Becket; Thomas W. Gannaway, both of Rochester, all of N.Y.

[73] Assignee: The Singer Company, New York, N.Y.

[21] Appl. No.: 974,635

[22] Filed: Dec. 29, 1978

[51] Int. Cl.² ............................................. G09B 19/00
[52] U.S. Cl. .................................. 35/29 R; 35/22 R; 324/66
[58] Field of Search ......................... 29/593, 701, 704; 35/10, 13, 19 A, 29 R, 22 R; 324/51, 66

[56] References Cited

U.S. PATENT DOCUMENTS

| | | | |
|---|---|---|---|
| 2,805,471 | 9/1957 | Lowden | 35/19 A UX |
| 3,163,926 | 1/1965 | Gray | 324/66 X |
| 3,169,305 | 2/1965 | Gray | 29/701 |
| 3,521,161 | 7/1970 | Kurata | 324/66 |
| 3,609,740 | 9/1971 | Paine | 324/66 X |
| 3,699,630 | 10/1972 | Tarbox | 29/704 X |
| 3,705,347 | 12/1972 | Tuller | 324/66 |
| 4,074,187 | 2/1978 | Miller | 324/66 X |

OTHER PUBLICATIONS

Amos E. Keyhart, "Road Test in Traffic" copyright 1947.

*Primary Examiner*—Harland S. Skogquist
*Attorney, Agent, or Firm*—Charles R. Lewis

[57] ABSTRACT

An electronics assembly evaluator for evaluating the skill and knowledge of a prospective electronics assembler. The evaluator provides the assembler with considerable amount of work to perform in the fabrication of a test circuit and a wire harness while maintaining a completely safe electrical environment independent of the work performed by the assembler. The evaluator includes a device for determining the accuracy as well as the quality of the work performed.

6 Claims, 4 Drawing Figures

4,198,768

ELECTRONICS ASSEMBLY EVALUATOR

BACKGROUND OF THE INVENTION

This invention relates to testing and more particularly to the evaluation of a persons skill and knowledge with respect to electronics wiring.

When an employer has the need to hire a person for electronics wiring, the employer needs to know whether that person possesses the requisite amount of skill and knowledge to perform the task. These skills include the ability to follow intricate instructions without committing errors, the ability to solder to a reasonable standard, and the ability to recognize and discern various electronic components. Many employers use a system wherein the prospective electronics assembler after passing a written test, is employed on a probationary basis for a period of time, say three months, during which time this person's performance is closely scrutinized. At the end of this period, a decision is made whether to release the person or place him (her) on the permanent payroll. Although this type of system is effective in acquiring persons with the requisite amount of skill, it is, at the same time, costly.

SUMMARY OF THE INVENTION

An object of the present invention is to offer an employer an alternative to the above mentioned system which is significantly less expensive. As a minimum, the invention may be used in addition to the probationary system as a pre-screening, thereby reducing the rate of drop-out.

Another object of this invention is to provide a hands-on test of the participant wherein he (she) is required to perform a significant amount of wiring and assembly using a variety of components.

Another object of this invention is to provide a hands-on test of the participant which is completely safe, that is, regardless of how the test portion is wired, the electrical currents present never rise above a safe limit.

These objects are achieved in an electronics assembly evaluator having a wire harness assembly board, a printed circuit board, a plurality of electronic components to be mounted on the printed circuit board, step by step instructions for assembling the wire harness and the printed circuit board and interconnecting the two, a power supply module for energizing the wire harness and the printed circuit board including means for determining the integrity of the assembly, and an evaluation manual for establishing the work criteria and error standards for the electronics assembler.

In general, by using the invention, the assembler demonstrates the following skills and abilities: Medium finger dexterity, eye/hand coordination, motor coordination, form perception, color discrimination, ability to discriminate details among small parts, ability to concentrate on detailed work, appropriate work pace, and facility in adapting to a routine. In addition, depending upon the particular Electronics Assembly field, the assembler must be able to identify various electronic components as well as determine resistance values using the resistance color codes and be able to demonstrate his (her) proficiency in the use of the tools necessary for electronics assembly.

DESCRIPTION OF THE DRAWINGS

With the above and additional objects and advantages in mind as will hereinafter appear, the invention will be described with reference to the accompanying drawings in which.

DESCRIPTION OF THE PREFERRED EMBODIMENT

Figure 1:
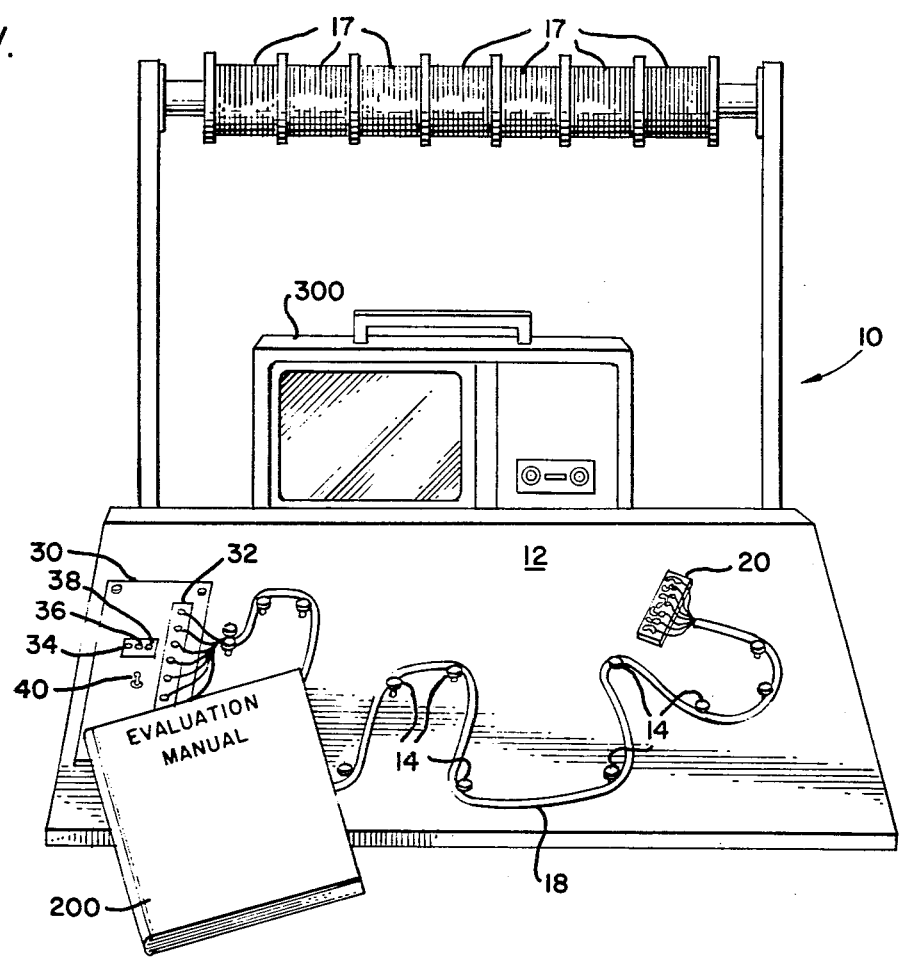
FIG. 1 is a front perspective view of the invention.
Figure 2:
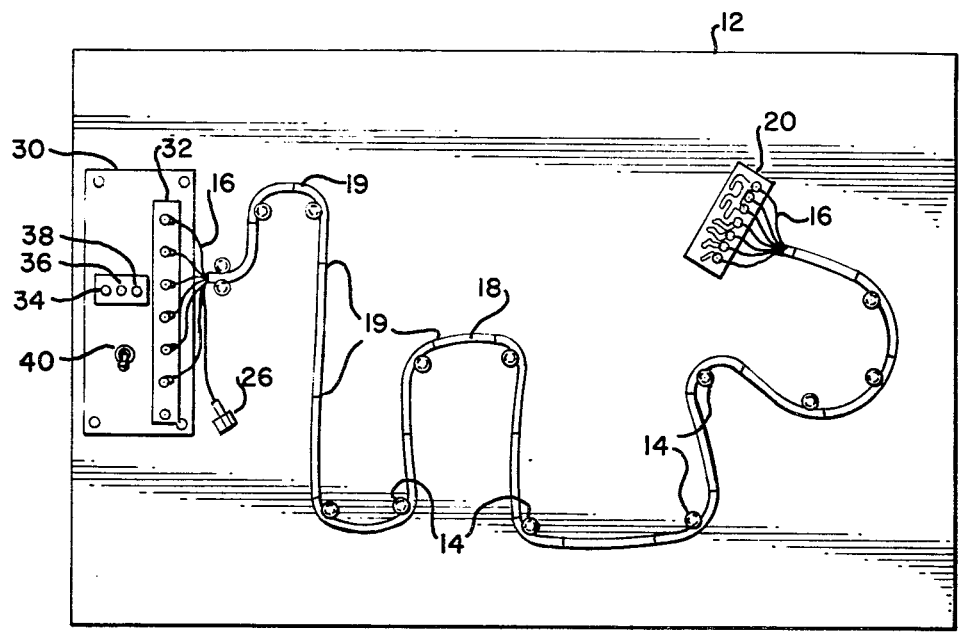
FIG. 2 is an elevational view of the invention.

In FIGS. 1 and 2 there is illustrated the electronics assembly evaluator 10 of this invention. The evaluator 10 includes a harness fabrication board 12 having a plurality of support post 14 around which wires 16, form a wire supply 17, may be strung in the fabrication of a wire harness 18. The wire harness 18 is secured with cable ties 19 and is shown terminating at one end thereof to a printed circuit board 20 having provisions thereon for receiving various electronic components (see FIG. 4). The other end of the wire harness 18 is shown having a spade lug 26 attached to the end of each of the wires 18 which are then connected to a power supply module 30.

The power supply module 30 includes a terminal strip 32 having terminals A–G for attaching the wire harness 18 thereto, and panel lights 34, 36 and 38 corresponding to the colors red, green and yellow. A switch 40 is also included for actuating the printed circuit board 20 wired by the assembler.

Figure 3:
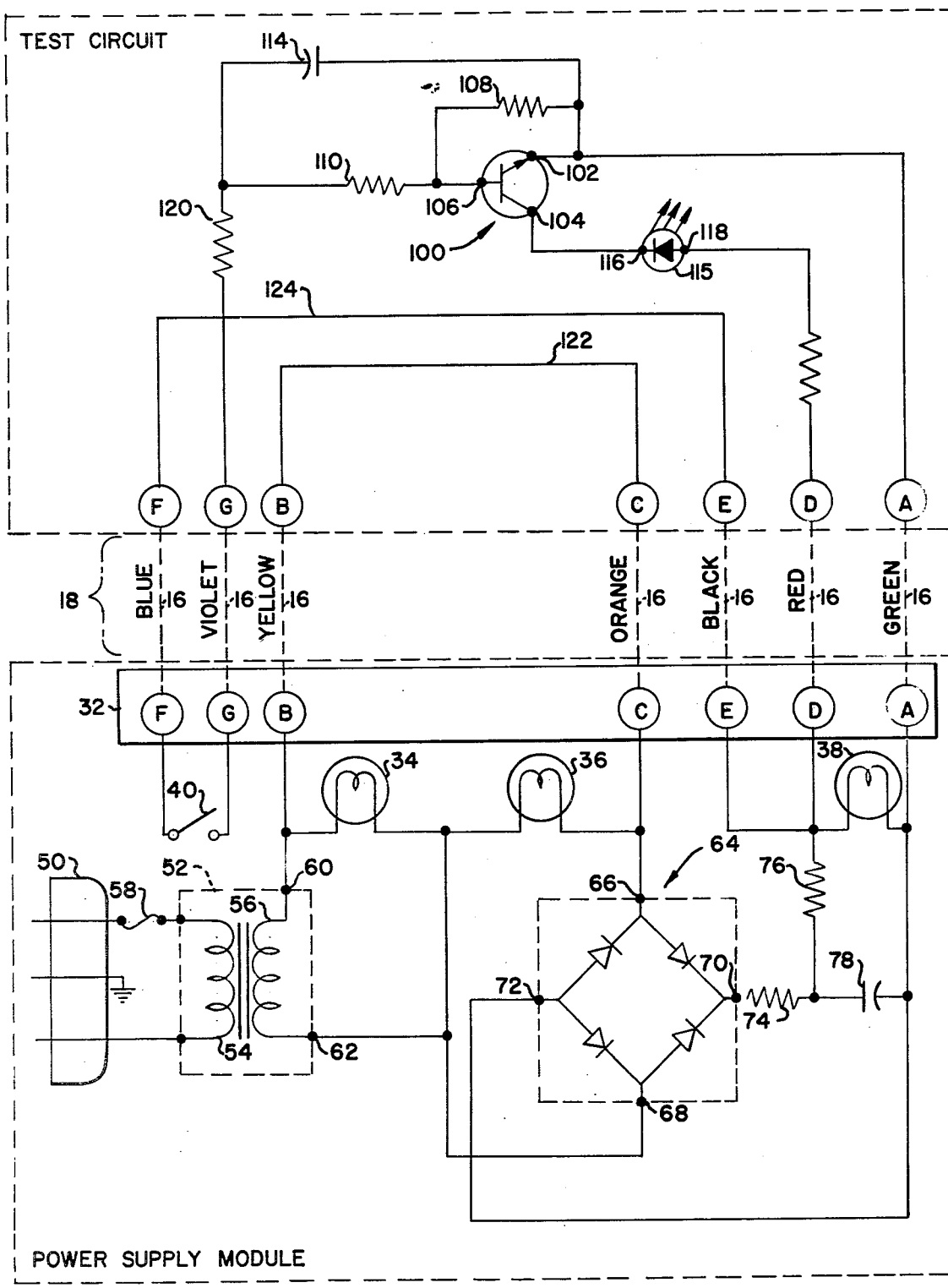
FIG. 3 is a schematic diagram of the power supply module of the invention and test circuit which is to be assembled.

In FIG. 3 there is shown a schematic diagram of the module 30. The module 30 receives electrical power through a standard AC plug 50. The voltage at the AC plug 50 is reduced from 115 volts to approximately 8 volts by a stepdown transformer 52 having a primary winding 54 and a secondary winding 56. The AC plug 50 is connected to the primary winding 54 in series with a fuse 58. The secondary winding 56 has, for identification purposes, a high end 60 and a low end 62. The panel light 34 is connected across the high and low ends 60 and 62 of the secondary winding 56. A rectifier 64 is illustrated in FIG. 2 as a diode bridge having input terminals 66 and 68 and output terminals 70 and 72. The low end 62 of the transformer 52 secondary winding 56 is connected to the rectifier 64 input terminal 68 while the panel light 36 is connected between the low end 62 of the transformer 52 secondary winding 56 and the rectifier 64 input terminal 66. The rectifier 64 output terminal 70 is connected to a first resistor 72 which is, in turn, connected to a second resistor 76. The panel light 38 is connected between the second resistor 76 and the rectifier 64 output terminal 72. A capacitor 78 is connected between the junction of the first and the second resistors 74 and 76 and the rectifier 64 output terminal 72.

The terminal strip 32 is shown as having the terminal A connected to the rectifier 64 output terminal 72, the terminal B connected to the high end 60 of the transformer 62 secondary winding 56, the terminal C connected to the rectifier 64 input terminal 66, and the terminals D and E connected at the junction of the second resistor 76 and the panel light 38. The terminals F and G of the terminal strip 32 are connected one to the other by the switch 40.

Also in FIG. 3, there is illustrated the schematic diagram for the test circuit when properly assembled on the printed circuit board 20 by the prospective electronics assembler. The test circuit includes contact pads A–G and a transistor 100 having an emitter 102, a collector 104 and a base 106. The emitter 102 is connected to the contact pad A. A first resistor 108 interconnects the emitter 102 and the base 106 of the transistor 100. The transistor 100 base 106 is connected to a second resistor 110 which is connected to a third resistor 112 which, in turn, is connected to the contact pad G. A capacitor 114 connects the transistor 100 emitter 102 to the junction of the second and third resistors 110 and 112. A light emitting diode (LED) 115 is shown having an enode 116 and a cathode 118. The LED 115 anode 116 is connected to the transistor 100 collector 104. The LED 115 cathode 118 is connected to a fourth resistor 120 which is in turn connected to contact pad D. The contact pads B and C are interconnected one to the other with a jumper wire 122 as are the contact pads E and F with a jumper wire 124.

Figure 4:
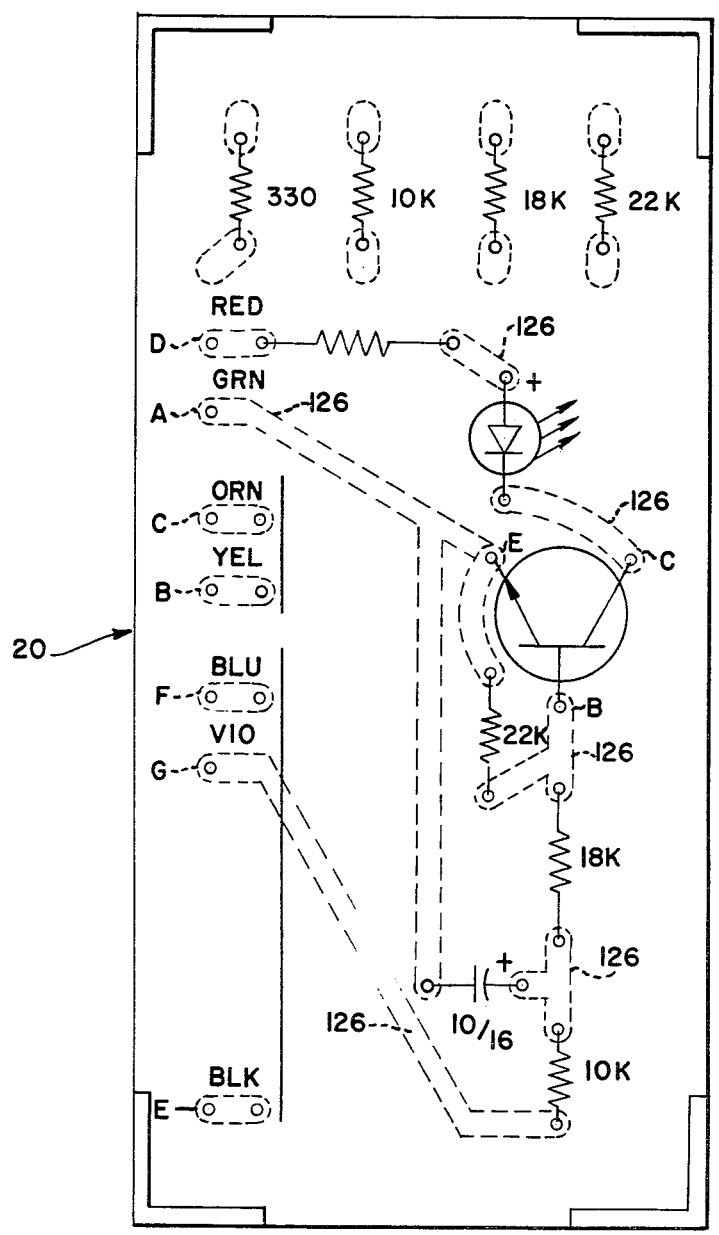
FIG. 4 is an elevational view of the printed circuit board on which the test circuit is assembled.

FIG. 4 shows the layout for the above-described electronic components on the printed circuit board 20. Conductive paths 126 (shown in phantom) are etched into the printed circuit board 20 for interconnecting the components.

In FIG. 1 there is also shown an evaluation manual 200 and an audio visual device 300 for giving instructions to the prospective electronics assembler as to the assembly of the printed circuit board 20 and the fabrication of the wire harness 18. Although, in this embodiment the audio visual device 300 is used as an instruction means, it should be pointed out that other means may be used, such as for example, instruction sheets.

The evaluation manual 200 contains criteria for rating the performance of the assembler. These criteria are listed in Table 1. Each of the factors listed therein has value to all areas of employment in the Electronic Assembly Field. The value of each factor, however, changes with the requirements of the specific job or occupational area. Therefore, an employer using this invention will need to assess the assembler's performance as it would pertain to the particular field of interest.

TABLE 1

|   |   | Errors Occurrences |
|---|---|---|
| A. | Harness Wiring Errors | |
|    | 1. Failure to thread the wire past all the support posts | 1 omission on each wire |
|    | 2. Insufficient wire remains to attach spade lugs to wires in such a way that the wires reach the terminals | 1/wire |
|    | 3. Cutting a wire any where except at the "Cut Here" line | 1 |
|    | 4. Wires in harness not strung tautly across support posts | 1 |
|    | 5. One or more wires missing. | 1 |
|    | 6. Unused wire not returned to its spool | 1 |
| B. | Cable Tie Errors | |
|    | 1. Too few or too many cable ties put in harness | 1 |
|    | 2. Cable Tie assembled backwards and thus unable to hold the cables | 1 |
|    | 3. Excess not cleanly trimmed from the cable tie | 1 |
| C. | Wire Stripping Errors | |
|    | 1. Stripping too much or too little insulation from the wires | 1 |
|    | 2. Using wrong tool to strip the wire | 1 |
| D. | Errors in Attaching Spade Lugs | |
|    | 1. Crimping is incomplete or messy; spade lug will not hold to the wire | 1 |
|    | 2. Spade lugs are attached to both ends of the wire | 1 |
| E. | Errors in Mounting Components | |
|    | 1. Resistor or other component is mounted in the wrong place on the printed circuit board | 1/component |
|    | 2. Component wires are untrimmed or poorly trimmed | 1 |
| F. | Errors in Soldering | |
|    | 1. Too much or too little solder used consistently | 1 error for either |
|    | 2. Unsafe use of soldering iron | 1 |

The evaluation manual 200 further contains information as to set-up and maintenance of the invention. This set-up information includes the tools required to perform the test, including wire pliers, diagonal cutters, a screwdriver and a soldering iron, as well as the supplies required, namely, seven spools of color coded insulated stranded wire, cable ties, spade lugs, various resistors, transistors and sockets, printed circuit boards, capacitors, light emitting diodes and solder. The maintenance information covers the replacement of bulbs and fuses in the power supply and instructions as to the "tinning" of the soldering iron if needed.

In using the invention, the prospective assembler is instructed by the audio-visual device 300 to cut a piece of wire 16 from each of the seven cobs added insulated wire spools 17, and assemble the wires 16 into the wire harness 18 by lacing the wires 16 around the support posts 14 and binding the wires with the cable ties 19. The assembler is then directed to terminate one end of the harness 18 by stripping each of the wires 16 at one end thereof and crimping a space lug 26 to each of the striped ends of the wire 16. The harness 18 is then connected to the power supply module 30 by fastening the spade lugs 26 to the terminal A–G on the terminal strip 32, carefully following the color coding (see FIG. 3). The assembler is then instructed to strip the opposite ends of the wires 16.

After completing the above, the assembler is instructed to separate the resistors 180, 110, 112, and 114 from the rest of the electronic components and, by determining their appropriate resistance values, position and solder the resistors in place. It should be noted that four resistor locations along the top edge of the printed circuit board 20 in FIG. 4 are not a part of the test circuit but are there only for visual evaluation. The assembler is then instructed to position and solder in place the capacitor 114, the LED 115, the transistor 100, mounted in a socket (not shown) and the jumper wires 122 and 124 to the printed circuit board 20. Finally, the instructions direct the assembler to solder the stripped ends of the harness 18 wires 16 to the contact pads A–G on the printed circuit board 20, again, carefully following the color coding (see FIG. 3). The harness 18, when connected correctly, interconnects the contact pads A–G on the terminal strip 32 as shown in FIG. 3.

The power supply module 30 may be energized while the assembler connects the harness 18 to the printed circuit board 20. When the plug 50 is connected to a standard 115 volt AC source, the red panel light 34 should glow immediately. When the assembler converts the proper harness 18 wires 16 to the contact pads A, B and C on the printed circuit board 20, electrical power from the transformer 52 secondary winding 56 is applied to the rectifier 64 input terminals 66 and 68 by means of the jumper wire 122 causing the green panel light 36 to glow. The exciting of the rectifier 64 induces a DC voltage at the output terminals 70 and 72 thereof causing the yellow panel light 38 to glow. After the harness 18 wires 16 are soldered to all the contact pads A–G, DC voltage is applied across the transistor 100 cathode 104 to the anode 102 entering at the contact pad D and exiting at the contact pad A. When the switch 40 is actuated, the DC voltage is applied to the transistor 100 base 106 originating at the contact pad G. The DC voltage at the transistor 100 base 106 causes the transistor 100 to "turn on", allowing conductance between the collector 104 and the emitter 102 which, in turn, causes the LED 115 to glow.

To evaluate the assembler's performance, the evaluator observes whether all the panel lights 34, 36 and 38 and the LED 115 are lit. For example, if the assembler installed an additional jumper between the contact pads A and D on the printed circuit board 20, the DC voltage energizing the LED 115 would be shorted preventing the LED 115 from glowing. Also, the panel light 38 would be shorted and would not glow. Another example would be, if the jumper 122 was not installed, neither the rectifier 64 nor the panel light 36 would receive excitation. Since the rectifier 64 would not be excited, there would be no DC output to cause the panel light 38 to glow or to excite the LED 115. The evaluator then inspects the work performed by the assembler and rates him/her in accordance with the criteria set forth in Table 1.

By referring to FIGS. 1, 2 and 3, it is shown that only low level voltages are accessible to the prospective electronics assembler at the terminal strip 32. This is achieved through the use of the step-down transformer 52. Also, to limit the amount of current in the DC circuit the output of the rectifier 64 a load resistance, in the form of the resistor 76, is inserted in series therewith.

Using the invention, the assembler is able to handle all of the basic electronic components and his ability to recognize each may be evaluated.

Numerous alterations of the structure herein disclosed will suggest themselves to those skilled in the art. However, it is to be understood that the present disclosure relates to a preferred embodiment of the invention which is for purposes of illustration only and not to be construed as a limitation of the invention. All such modifications which do not depart from the spirit of the invention are intended to be included within the scope of the appended claims.

We claim:

1. An electronics assembly evaluator for determining the skill and knowledge of a prospective electronics assembler comprising:
   a wire harness fabrication board having a plurality of support spots around which wires may be strung in the fabrication of a wire harness;
   a printed circuit board to which said wire harness may be connected;
   a plurality of electronic components for mounting on said printed circuit board;
   means for supplying step-by-step instructions for the fabrication of said wire harness and the placement of said electronic components on said printed circuit board; and
   a power supply module to which said wire harness may also be connected for energizing said wire harness to said printed circuit board after said wiring instructions have been completed by said prospective electronics assembler, said module including means for determining whether said wire harness along with said printed circuit board have been assembled correctly.

2. The electronics assembly evaluator as set forth in claim 1 which further comprises:
   an evaluation manual containing work criteria and error standards for evaluating said prospective electronics assembler.

3. The electronics assembly evaluator as set forth in claim 2 wherein said means for supplying step-by-step instructions comprises an audio-visual device.

4. The electronics assembly evaluator as set forth in claim 2 wherein said means for supplying step-by-step instructions comprises printed sheets.

5. The electronics assembly evaluator as set forth in claims 3 or 4 wherein determining means in said power supply module comprises lamps arranged to glow at different stages of assembly.

6. The electronics assembly evaluator as set forth in claim 5 wherein one of said lamps is mounted on said printed circuit board by the assembler.

* * * * *